(12) United States Patent
Oguri et al.

(10) Patent No.: US 9,709,502 B2
(45) Date of Patent: Jul. 18, 2017

(54) MEASUREMENT DEVICE AND MEASUREMENT METHOD

(75) Inventors: Kazuyuki Oguri, Tokyo (JP); Tomohiro Endo, Tokyo (JP); Hidenobu Kawada, Tokyo (JP); Yasushi Kondo, Tokyo (JP); Takeshi Muranaka, Tokyo (JP)

(73) Assignee: Fujirebio Inc., Tokyo (JP)

( * ) Notice: Subject to any disclaimer, the term of this patent is extended or adjusted under 35 U.S.C. 154(b) by 336 days.

(21) Appl. No.: 14/001,110

(22) PCT Filed: Feb. 14, 2012

(86) PCT No.: PCT/JP2012/000956
§ 371 (c)(1),
(2), (4) Date: Aug. 22, 2013

(87) PCT Pub. No.: WO2012/114675
PCT Pub. Date: Aug. 30, 2012

(65) Prior Publication Data
US 2013/0323758 A1 Dec. 5, 2013

(30) Foreign Application Priority Data

Feb. 22, 2011 (JP) ................................. 2011-036428

(51) Int. Cl.
*G01N 35/02* (2006.01)
*G01N 21/76* (2006.01)
(Continued)

(52) U.S. Cl.
CPC ........... *G01N 21/76* (2013.01); *G01N 35/025* (2013.01); *G01N 35/0098* (2013.01); *G01N 2035/0455* (2013.01); *G01N 2035/0458* (2013.01)

(58) Field of Classification Search
CPC .... G01N 35/02; G01N 2001/185; G01N 1/18; G01N 2001/2007
See application file for complete search history.

(56) References Cited

U.S. PATENT DOCUMENTS 4,699,766 A  10/1987 Yamashita
5,178,834 A * 1/1993 Kagayama ........... G01N 35/021
                                                    422/63

(Continued)

FOREIGN PATENT DOCUMENTS

CN  101324631 A  12/2008
CN  101452004 A   6/2009

(Continued)

OTHER PUBLICATIONS

English Translation of Office Action; Dec. 2, 2014; 2 pages.

*Primary Examiner* — Rebecca Martinez
(74) *Attorney, Agent, or Firm* — Reinhart Boerner Van Deuren P.C.

(57) ABSTRACT

A measurement device that includes a plurality of lines for conveying a reaction container containing a sample and measures a predetermined material included in the sample while conveying the reaction container by the plurality of lines, wherein the plurality of lines include: a first reaction line for conveying a reaction container at a first convey speed; a second reaction line for conveying a reaction container at a second convey speed; and a measurement line for measuring a predetermined material included in a sample reacted with a reagent within the reaction container in the first reaction line and a sample reacted with a reagent within the reaction container in the second reaction line, the measurement line conveying the reaction containers at a third convey speed that is higher than the first convey speed and the second convey speed.

7 Claims, 7 Drawing Sheets

(51) Int. Cl.
    *G01N 35/00*     (2006.01)
    *G01N 35/04*     (2006.01)

(56) References Cited

U.S. PATENT DOCUMENTS 5,538,849 A * 7/1996 Uematsu et al. ............ 435/6.19
2008/0311678 A1 12/2008 Ootani et al.

FOREIGN PATENT DOCUMENTS

| | | |
|---|---|---|
| JP | S61274268 A | 12/1986 |
| JP | 04-047268 A | 2/1992 |
| JP | 04-350561 A | 12/1992 |
| JP | 10-038892 A | 2/1998 |

* cited by examiner

MEASUREMENT DEVICE AND MEASUREMENT METHOD

TECHNICAL FIELD

The present invention relates to a measurement device and a measurement method for measuring a predetermined material included in a sample while conveying a reaction container containing the sample.

BACKGROUND ART

Conventionally, various measurement devices and measurement methods have been developed for separating and identifying a predetermined material to be measured (hereinafter referred to as a target material) from a sample including a plurality of materials and analyzing the target material. For example, an immunoassay method is used for measuring a target material by dispensing to a sample a reagent including an antibody that selectively combines with the target material only, causing the target material included in the sample to combine with the antibody in the reagent, and quantitatively detecting a complex produced by the combination, utilizing a phenomenon such as chemiluminescence, fluorescence, absorption, scattering or the like. Specifically, such immunoassay methods include EIA (Enzyme Immunoassay), FIA (Fluorescence Immunoassay) and the like.

As a measurement device for performing such a measurement, a measurement device has been proposed in which a sample and a reagent are separately dispensed to a reaction container then the sample is reacted with the reagent within the reaction container to perform a measurement. Such a measurement device includes a conveyer line for conveying a plurality of reaction containers and performs various steps for reaction and measurement while conveying the plurality of reaction containers in the conveyer line at a predetermined convey speed.

Note that the reaction time required for reacting a sample with a reagent may depend on a combination of type and concentration (dilution) of the sample and the reagent. So, conventionally, a measurement device has also been proposed that can accommodate measurements with different reaction times. For example, an immunoanalytical device described in Patent Document 1 includes an inner reaction line and an outer reaction line placed in the same plane and can convey reaction containers in the inner reaction line and the outer reaction line at speeds different from each other.

PRIOR ART DOCUMENT

Patent Document

[Patent Document 1] JP-A-4-47268

SUMMARY OF THE INVENTION

Problems to be Solved by the Invention

It is an object of the present invention to solve the problems of the above mentioned prior arts.

Means for Solving the Problems

One aspect of the present invention provides a measurement device that includes a plurality of lines for conveying a reaction container containing a sample and measures a predetermined material included in the sample while conveying the reaction container by the plurality of lines, wherein the plurality of lines include: a reaction line for reacting the sample with a reagent within the reaction container, the reaction line conveying the reaction container at a predetermined convey speed; and a measurement line for measuring the predetermined material included in the sample reacted with the reagent within the reaction container in the reaction line, the measurement line conveying the reaction container conveyed from the reaction line at a predetermined convey speed that is higher than the convey speed.

BRIEF DESCRIPTION OF THE DRAWINGS

FIG. 4(a) shows a placement of cuvettes in a mode that is a mixture of a normal mode and a time reduction mode at equal rate. FIG. 4(b) shows a placement of cuvettes in the time reduction mode only. FIG. 4(c) shows a placement of cuvettes in the normal mode only.

Before explaining embodiments of the present inventions, exemplary problems to be solved by the embodiments will be explained.

For measurement items with different reaction times, in the device described in the Patent Document 1, samples are dispensed to reaction containers provided in the inner reaction line and the outer reaction line, then the reaction containers are conveyed at speeds different between the inner reaction line and the outer reaction line, and then target materials produced in the inner reaction line and the outer reaction line are measured in a measurement unit provided lateral to the inner reaction line and the outer reaction line. In this case, since a sample may be dispensed to only one of the inner reaction line and the outer reaction line depending on a measurement method, a reaction container with no sample dispensed may exist on the inner reaction line and the outer reaction line, which is a problem of decreasing the throughput of the inner reaction line and the outer reaction line in spite of providing two lines.

In other words, in order to maximize the throughput of the inner reaction line and the outer reaction line, all of the reaction containers on the reaction lines should be used with no vacancy, which occurs only when the ratio of the number of tests of the inner reaction line and the outer reaction line is 1:1. However, in the device described in the Patent Document 1, when items with different reaction times are measured, all of the reaction containers in the inner reaction line and the outer reaction line may not be used depending on a combination of the items with a vacancy in either the inner reaction line or the outer reaction line, which decreases the throughput.

In order to avoid such decrease in the throughput, it is necessary to provide two samplers for separately supplying samples to the reaction containers on the respective reaction lines, which inevitably requires the device to be larger and the control to be more complicated.

In order to solve the above-described problem, it is an object of the present embodiment to provide a measurement device and a measurement method in which an immune reaction line for conveying a reaction container and a measurement line for conveying a reaction container at a speed higher than that of the reaction line are combined to allow the throughput to be prevented from decreasing and the device to be prevented from becoming larger even in measuring a combination of measurement items with different reaction times, with no vacancy in the reaction lines.

MODE FOR CARRYING OUT THE INVENTION

Embodiments of the invention are described below in detail with reference to the accompanying drawings. First, a basic concept common to the embodiments is described in [I], then the embodiments are specifically described in [II], and finally, variations of the embodiments are described in [III]. However, it should be appreciated that the invention is not limited to the embodiments.

[I] BASIC CONCEPT COMMON TO EMBODIMENTS

First, a basic concept common to the embodiments is described. A measurement device in accordance with the embodiments includes a plurality of lines for conveying a reaction container containing a sample and measures a predetermined material included in the sample while conveying the reaction container by the plurality of lines. Furthermore, a measurement method is for measuring a predetermined material included in a sample while conveying a reaction container containing the sample.

The measurement device and the measurement method in accordance with the embodiments can be specifically applied to any appropriate field unless otherwise specified. For example, in the medical field, the measurement device and the measurement method can be applied to an automatic immunoassay device and an automatic immunoassay method for separating and identifying a predetermined material to be measured from a sample including a plurality of target materials and analyzing the predetermined material. In the following embodiments, the invention is described as applied to an automatic immunoassay device and an automatic immunoassay method for performing analysis of a sample, such as blood, using an EIA (Enzyme Immunoassay) that uses an enzyme as a labeled material.

This type of measurement devices and measurement methods include: a device and method in which a reaction container is washed after a measurement and reused for another measurement; and a device and method in which a disposable reaction container (hereinafter referred to as a cuvette) is disposed of after a measurement. The invention can be applied to the both types of device and method. However, in the following description, the invention is described as applied to the device and method using a cuvette.

Furthermore, this type of measurement methods include one-step method, delay one-step method, two-step method, dilution two-step method, competition method and the like. As a solid phase used for the measurement, various magnetic particles, polystyrene particles, latex particles and the like can be used. The invention can be applied to any of these methods. However, in the following description, the invention is described as applied to a dilution two-step method for measuring an antigen included in a sample using magnetic particles as a solid phase, an enzyme as a labeled material, and a luminescent substrate as a substrate. Generally, the dilution two-step method performs the following steps in this order: 1) a "pretreatment step" in which pretreatment, such as dilution, is performed on a sample; 2) a "first reaction step" in which, by, for example, dispensing a first reagent to the sample, a target material (antigen) included in the sample is reacted with a first antibody coupled to magnetic particles, to cause the target material to be coupled to the first antibody; 3) a "second reaction step" in which, by, for example, dispensing a second reagent (enzyme-labeled antibody) to the complex with magnetic particles produced in the first reaction step, the complex is reacted with the enzyme-labeled antibody (a second antibody) to cause the complex to be coupled to the enzyme-labeled antibody (the second antibody); 4) an "enzyme reaction step" in which, by, for example, dispensing a luminescent substrate to the complex with the labeled antibody produced in the second reaction step, the enzyme coupled to the magnetic particles to form a complex is reacted with the luminescent substrate; and 5) a "measurement step" in which the amount of chemiluminescence produced in the enzyme reaction step is measured. As a result, the amount of the target material (antigen) can be determined from the luminescence amount obtained in the measurement step.

Generally, one feature of the measurement device in accordance with the embodiments is in that: 1) a plurality of reaction lines for reacting a sample with a reagent within a reaction container is separated from a measurement line for measuring a target material from the samples in the reaction containers reacted in the reaction lines; and 2) furthermore, the convey speed of the reaction containers in the measurement line is set to be higher than the convey speed of the reaction containers in the plurality of reaction lines. Separating the plurality of reaction lines from the measurement line in this way allows the convey speed of the reaction containers in the reaction steps to be different from the convey speed of the reaction containers in the measurement step. Furthermore, setting the convey speed of the reaction containers in the measurement line to be higher than the convey speed of the reaction containers in the plurality of reaction lines allows the throughput of the measurement line to be higher than the throughput of the reaction lines, which allows the reaction containers after the reaction in the reaction lines to be transferred to the measurement line without delay, thereby allowing the overall throughput to be prevented from decreasing.

Hereinafter, "throughput" means the number of cuvettes per unit time (unit: cuvettes per hour) discharged from the reaction line or the measurement line after treatment. Here, "throughput decreases" means that the throughput of a reaction step falls below the maximum throughput of the reaction step. For example, when a maximum throughput of a reaction line is 240 cuvettes per hour and an actual throughput of the reaction line is lower than 240 cuvettes per hour at the maximum, the throughput is considered to be decreasing. In other words, in this case, when the actual throughput of the reaction line is 240 cuvettes per hour at the maximum, the throughput is considered to be prevented from decreasing.

[II] SPECIFIC DESCRIPTION OF EMBODIMENTS

Next, the embodiments are specifically described. The measurement devices and the measurement methods in accordance with the embodiments are described in order.

First Embodiment

First, a first embodiment is described. The first embodiment is such that a first reaction line and a second reaction line are provided on respective disk-shaped tables different from each other.

(Configuration—Overall)

Figure 1:
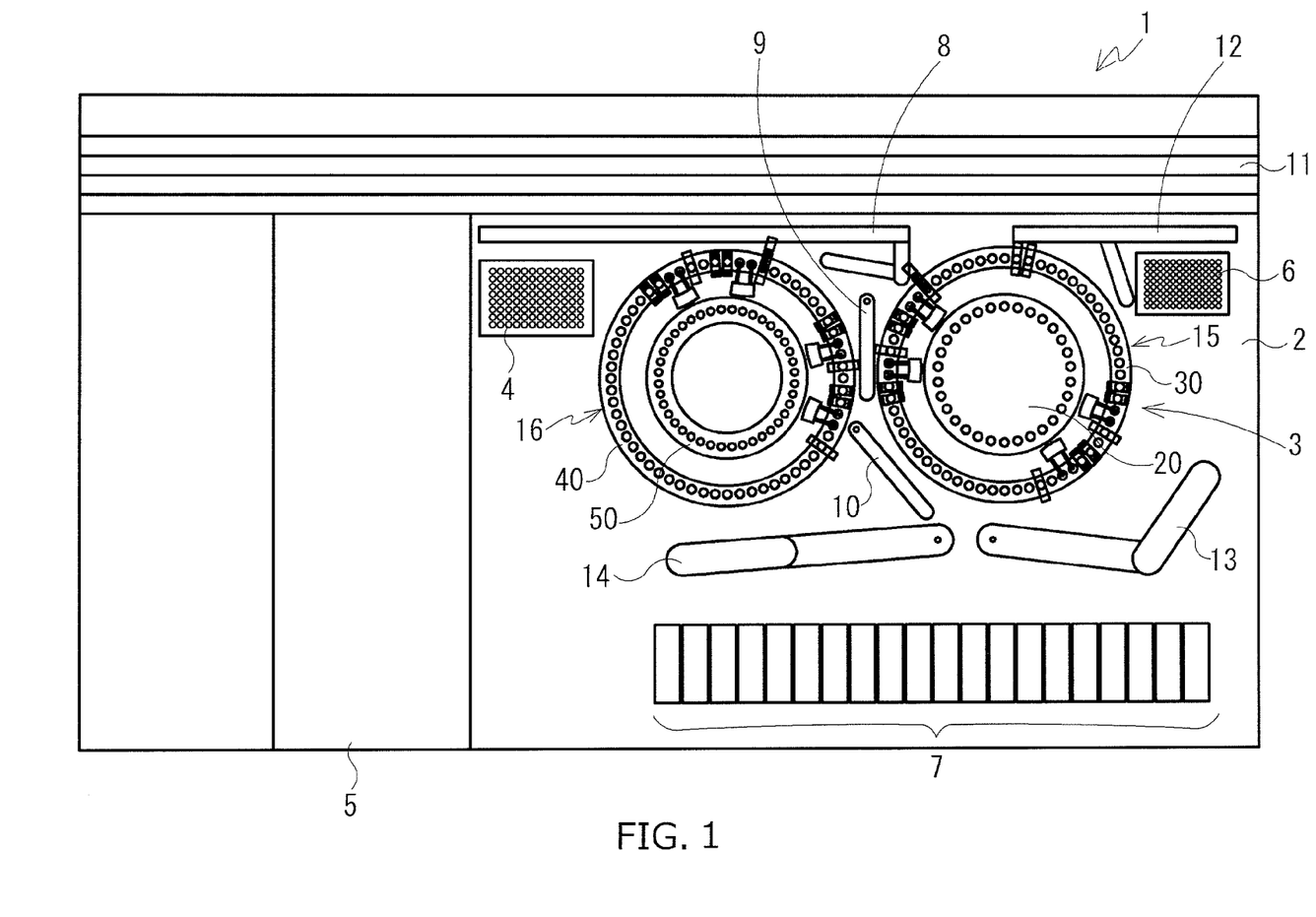
FIG. 1 A main part plan view of a measurement device in accordance with a first embodiment of the invention.

First, the overall configuration of the measurement device is described. FIG. 1 is a main part plan view of a measurement device in accordance with the first embodiment. The measurement device 1 is an automatic immunoassay device. Generally, the measurement device 1 is configured such that a measurement mechanism 3 is placed on a base surface 2. The measurement mechanism 3 conveys a cuvette (not shown) to a plurality of predetermined positions in order, then performs a measurement by performing various predetermined operations at these positions, and then disposes of the cuvette after the measurement. Note that the configuration of the measurement device 1 may be the same as that of a known automatic immunoassay device unless otherwise specified.

The measurement mechanism 3 includes a cuvette feeder 4, a sample feeder 5, a tip feeder 6, a reagent containing space 7, a first cuvette conveyer 8, a second cuvette conveyer 9, a third cuvette conveyer 10, a sample conveyer 11, a tip conveyer 12, a first reagent dispenser 13, a second reagent dispenser 14, a first table 15 and a second table 16.

The cuvette feeder 4 is a containing/lining-up means for containing and lining up a plurality of cuvettes before use and, for example, is configured as a part feeder. The sample feeder 5 is a sample containing/lining-up means for containing and lining up a plurality of samples before measurement and, for example, is configured as a sample rack loader for conveying a rack (not shown) containing a plurality of samples lined up. The tip feeder 6 is a tip containing/lining-up means for containing and lining up a disposable tip for drawing a sample and, for example, is configured as a part feeder. The reagent containing space 7 is a reagent containing means for containing containers lined up containing a plurality of reagents (in this example, a magnetic particle solution bottle, a conjugate solution bottle, a pretreatment solution bottle, a sample dilute solution bottle and the like, all of them not shown) and particularly has a function of mixing the content of the magnetic particle solution bottle.

The first cuvette conveyer 8 is a cuvette conveying means for conveying a cuvette contained in the cuvette feeder 4 to a pretreatment line 20 and a first reaction line 30 described later. The second cuvette conveyer 9 is a cuvette conveying means for conveying a cuvette from the first reaction line 30 and a second reaction line 40 to a measurement line 50 described later. The third cuvette conveyer 10 is a cuvette conveying means for conveying a cuvette from the first reaction line 30 to the second reaction line 40. The first cuvette conveyer 8, the second cuvette conveyer 9 and the third cuvette conveyer 10 are configured as a known robot arm using a step motor or the like.

The sample conveyer 11 is a sample conveying means for conveying a rack from the sample feeder 5 to a predetermined sample dispensing position (near the tip conveyer 12) and, for example, is configured as a sample rack loader for conveying a rack (not shown) containing a plurality of samples lined up. The tip conveyer 12 takes a tip contained in the tip feeder 6, then draws a sample through the tip from the rack conveyed by the sample conveyer 11, and then discharges the drawn sample to a cuvette placed in the pretreatment line 20 and the first reaction line 30. The first reagent dispenser 13 dispenses a reagent from the container contained in the reagent containing space 7 to a cuvette placed in the pretreatment line 20, the first reaction line 30 and the second reaction line 40. The second reagent dispenser 14 dispenses a reagent from the container contained in the reagent containing space 7 to a cuvette placed in the first reaction line 30 and the second reaction line 40. The tip conveyer 12, the first reagent dispenser 13 and the second reagent dispenser 14 are configured by combining a drawing mechanism using a pump with a known robot arm using a step motor or the like.

The first table 15 is a conveyer line for conveying a plurality of cuvettes and includes the pretreatment line 20 provided in the inner periphery and the first reaction line 30 provided in the outer periphery. The pretreatment line 20 is a line for performing pretreatment and dilution on a sample. The first reaction line 30 is a line for reacting a sample with magnetic particles or reacting a product of the reaction between the sample and the magnetic particles with a labeled antibody. The pretreatment line 20 and the first reaction line 30 are formed to be respective ring-shaped bodies placed concentrically to each other. The ring-shaped bodies include a plurality of holes formed thereon into which a cuvette is removably inserted from above. The ring-shaped bodies can be rotated at convey speeds (rotation speeds) the same as or different from each other by a known drive mechanism (not shown) using a pulse motor or the like. The pretreatment line 20 and the first reaction line 30 are described later in detail.

The second table 16 is a conveyer line for conveying a plurality of cuvettes and includes the second reaction line 40 provided in the outer periphery and the measurement line 50 provided in the inner periphery. The second reaction line 40 is a line for reacting a product of the reaction between the sample and the magnetic particles with a labeled antibody. The measurement line 50 is a line for detecting an enzyme reaction between a labeled antibody and a substrate and detecting the light amount of light generated by chemiluminescence from a product of the enzyme reaction. The second reaction line 40 and the measurement line 50 are formed to be respective ring-shaped bodies placed concentrically to each other. The ring-shaped bodies include a plurality of holes formed thereon into which a cuvette is removably inserted from above. The ring-shaped bodies can be rotated at convey speeds (rotation speeds) the same as or different from each other. The second reaction line 40 and the measurement line 50 are described later in detail.

(Configuration—Conveyer Line)

Figure 2:
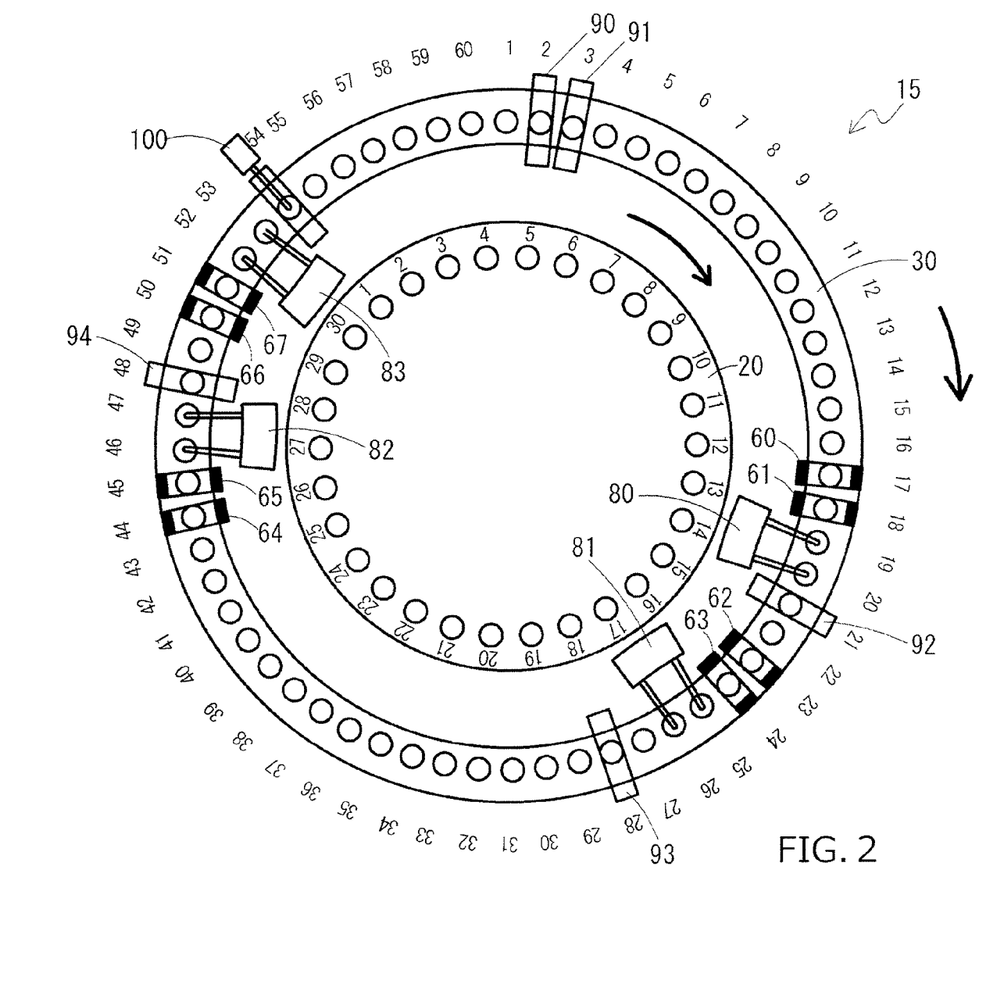
FIG. 2 An enlarged plan view of a first table.
Figure 3:
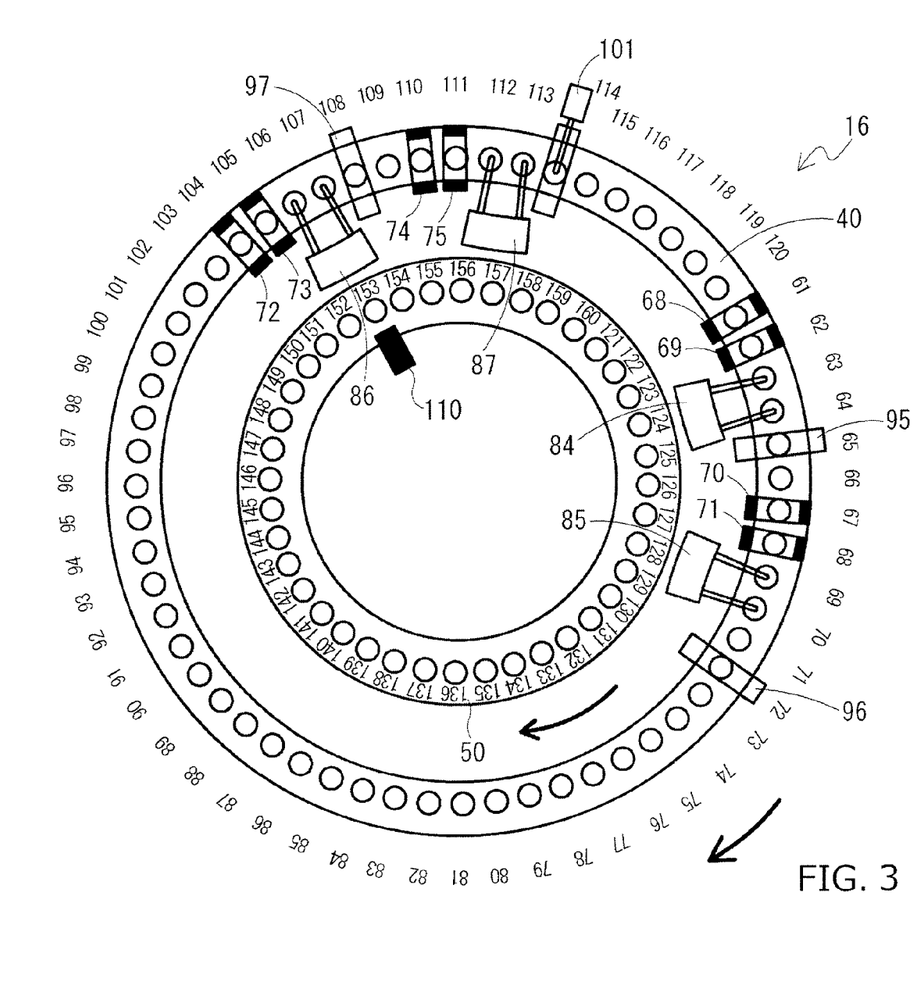
FIG. 3 An enlarged plan view of a second table.

Next, the conveyer lines are described in more detail. FIG. 2 is an enlarged plan view of the first table 15. FIG. 3 is an enlarged plan view of the second table 16. On the pretreatment line 20, 30 cuvettes can be placed at regular intervals in a ring shape. These cuvettes are intermittently conveyed illustrated clockwise at 15 second intervals, so they rotate one revolution in 450 seconds (=30 by 15 seconds). The following description is made, as appropriate, with the positions of the cuvettes on the pretreatment line 20 (the positions at which the cuvettes are temporarily halted in intermittent conveying, the same shall apply hereinafter) attached with a number that is incremented by one clockwise from P1 (however, for simplified illustration, in the drawings, "P" is omitted and leader line is further omitted to distinguish the number from a reference numeral with the same number for another component, the same shall apply to the first reaction line 30, the second reaction line 40 and the measurement line 50). Note that the pretreatment line may work in any rotation direction (clockwise or counterclockwise).

On each of the first reaction line 30 and the second reaction line 40, 60 cuvettes can be placed at regular intervals in a ring shape. These cuvettes are intermittently conveyed illustrated clockwise at 15 second intervals, so they rotate one revolution in 900 seconds (=60 by 15 seconds). The following description is made, as appropriate, with the positions of the cuvettes on the first reaction line 30 attached with a number that is incremented from the initial position P1 to the final position P60 and with the positions of the cuvettes on the second reaction line 40 attached with a number that is incremented from the initial position P61 to the final position P120.

On the first reaction line 30 and the second reaction line 40, a plurality of magneto collectors 60-75, wash solution dischargers/drawers 80-87, mixers 90-97 and substrate dispensers 100, 101 are provided as shown. The magneto collectors 60-75 apply a magnetic force of a magnet from the outside to a cuvette to cause magnetic particles to be collected to the inner wall surface of the cuvette. The wash solution dischargers/drawers 80-87 discharge a wash solution fed from a wash solution tank (not shown) into a cuvette through a pump and draw the discharged wash solution through a pump to wash off magnetic particles in the cuvette. The mixers 90-97 rotate a cuvette about the center axis of the cuvette by a motor or vibrate the cuvette by a vibrator to disperse magnetic particles in the cuvette. The substrate dispensers 100, 101 dispense a substrate solution fed from a substrate solution tank (not shown) to a cuvette through a pump and, after dispensing the substrate solution, mix the content of the cuvette as with the mixers 90-97.

On the measurement line 50, 40 cuvettes can be placed at regular intervals in a ring shape. These cuvettes are intermittently conveyed illustrated clockwise at 7.5 second intervals, so they rotate one revolution in 300 seconds (=40 by 7.5 seconds). The following description is made, as appropriate, with the positions of the cuvettes on the measurement line 50 attached with a number that is incremented from the initial position P121 to the final position P160. The measurement line 50 includes a measurement unit 110 provided at the position P153. The measurement unit 110 measures the light amount of weak light generated by chemiluminescence from a product of an enzyme reaction, and, more particularly, photocounts the amount of photons using a photoelectrical amplifier.

Although, for convenience of explanation, the conveyer lines are broadly divided into the pretreatment line 20, the first reaction line 30, the second reaction line 40 and the measurement line 50, these line names are not intended to strictly define treatments performed in the respective lines. For example, in the first reaction line 30, a treatment other than the reaction-related treatment (e.g., part of pretreatment) may also be performed. Or the treatment of the first reaction step may also be performed in a line other than the first reaction line 30.

(Measurement Method)

Next, a measurement method performed using the measurement device 1 configured as above is described. Practically, this measurement method is programmed as a measurement program that is installed in a storage unit (not shown) of the measurement device 1 via any suitable recording medium (not shown) or via any suitable network, such as the Internet. Then, when a control unit (not shown) of the measurement device 1 accepts a predetermined start instruction from a user via an input means (not shown), the control unit automatically performs the measurement method by interpreting and executing the measurement program.

According to this measurement method, measurement can be performed either in a normal mode or in a time reduction mode, or measurement can be performed in a mode that is a mixture of the normal mode and the time reduction mode. The following description is for performing measurement in a mode that is a mixture of the normal mode and the time reduction mode.

The normal mode is a mode in which a sample is reacted with a reagent within a reaction container in a predetermined reaction time. Generally, the first reaction step is performed in the first reaction line 30 for about 8 minutes, then the second reaction step is performed in the second reaction line 40 for about 8 minutes, and then the enzyme reaction step is performed in the measurement line 50 for about 4 minutes, so, the reaction in the normal mode is performed for about 20 minutes in total. More specifically, in the normal mode, "the pretreatment step" is performed from the position P1 to the position P30 of the pretreatment line 20; "the first reaction step" is performed from the position P1 to the position P33 of the first reaction line 30 for about 8 minutes (=32 intermittent intervals by 15 seconds); "the second reaction step" is performed from the position P72 to the position P103 of the second reaction line 40 for about 8 minutes (=31 intermittent intervals by 15 seconds); and "the enzyme reaction step" is performed from the position P121 to the position P152 of the measurement line 50 for about 4 minutes (=31 intermittent intervals by 7.5 seconds). Then, "the measurement step" is performed at the position P153 of the measurement line 50.

On the other hand, the time reduction mode is a mode in which reaction is performed in a predetermined reaction time shorter than that of the normal mode, using a reagent specifically for the time reduction mode. Generally, the first reaction step is performed in the first reaction line 30 for 4 minutes, then the second reaction step is performed in the first reaction line 30 for 4 minutes, and then the enzyme reaction step is performed mainly in the measurement line 50 for 4 minutes, so, the reaction in the time reduction mode is performed for 12 minutes in total. More specifically, in the time reduction mode, "the pretreatment step" is performed from the position P1 to the position P30 of the pretreatment line 20; "the first reaction step" is performed from the position P1 to the position P17 of the first reaction line 30 for 4 minutes (=16 intermittent intervals by 15 seconds); "the second reaction step" is performed from the position P28 to the position P44 of the first reaction line 30 for 4 minutes (=16 intermittent intervals by 15 seconds); and "the enzyme reaction step" is performed from the position P121 to the position P152 of the measurement line 50 for about 4 minutes (=31 intermittent intervals by 7.5 seconds). Then, "the measurement step" is performed at the position P153 of the measurement line 50.

However, which steps the treatments at the positions as described above belong to may vary depending on which steps the functions of the treatments are considered to belong to. Among others, collecting magnetic particles, washing a cuvette and mixing the content of a cuvette may be considered to belong to a step immediately before or after the above-described step.

In this example, as described above, the convey speed of a cuvette in the first reaction line 30 (a first convey speed) is set to one step per 15 seconds (hereinafter written as "15 second intervals"); the convey speed of a cuvette in the second reaction line 40 (a second convey speed) is set to 15 second intervals; and the convey speed of a cuvette in the measurement line 50 (a third convey speed) is set to one step per 7.5 seconds (hereinafter written as "7.5 second intervals") (which is a common multiple of the first convey speed and the second convey speed or an integer multiple of the first convey speed and the second convey speed). However, the description of the intermittent conveying of a cuvette at 15 second intervals in the first reaction line 30 and the second reaction line 40 and the intermittent conveying of a cuvette at 7.5 second intervals in the measurement line 50 is omitted.

(Measurement Method—Normal Mode)

First, the measurement method in the normal mode is described. Specifically, in the normal mode, a new cuvette is fed to the position P27 of the pretreatment line 20 by the cuvette conveyer 8. Then, a dilute solution is dispensed by the reagent dispenser 13 at the position P30. Then, a new tip is taken from the tip feeder 6 at the position P1, then a sample is drawn from the rack conveyed by the sample conveyer 11, then the sample is dispensed to the cuvette with the dilute solution therein, and then the content of the cuvette is mixed.

At the same time, a new cuvette is fed to the position P58 of the first reaction line 30 from the cuvette feeder 4 by the first cuvette conveyer 8. Then, at the position P60, a magnetic particle solution is dispensed to the cuvette from a magnetic particle solution bottle placed in the reagent containing space 7 by the first reagent dispenser 13. Then, at the position P1, the diluted sample is drawn from the position P1 of the pretreatment line 20, then the drawn sample is discharged to the cuvette, and then the content of the cuvette is mixed at the positions P2 and P3 by the mixers 90 and 91, respectively.

Then, at the position P33, the cuvette is conveyed to the position P120 of the second reaction line 40 by the third cuvette conveyer 10. Then, at the positions P61 and P62 of the second reaction line 40, the magnetic particles within the cuvette are collected by the magneto collectors 68 and 69 respectively. Then, at the positions P63 and P64, a wash solution is discharged and drawn within the cuvette by the washer 84 to wash off the magnetic particles. Then, at the position P65, the content of the cuvette is mixed by the mixer 95, then, at the positions P67 and P68, the magnetic particles are collected again by the magneto collectors 70 and 71, respectively, and then, at the positions P69 and P70, the magnetic particles are washed off by the washer 85.

Then, at the position P71, a conjugate solution is dispensed to the cuvette from a conjugate solution bottle placed in the reagent containing space 7 by the second reagent dispenser 14, then, at the position P72, the content of the cuvette is mixed by the mixer 96, then, at the positions P104 and P105, the magnetic particles are collected by the magneto collectors 72 and 73, respectively, and then, at the positions P106 and P107, the magnetic particles are washed off again by the washer 86. Similarly, at the position P108, the content of the cuvette is mixed by the mixer 97, then, at the positions P110 and P111, the magnetic particles are collected by the magneto collectors 74 and 75, respectively, and then, at the positions P112 and P113, the magnetic particles are washed off again by the washer 87.

Then, at the position P114, a substrate solution is dispensed to the cuvette by the substrate dispenser 101, then the content of the cuvette is mixed to disperse the magnetic particles, then, at the position P115, the cuvette is conveyed to the position P121 of the measurement line 50 by the second cuvette conveyer 9, then, at the positions P121 to P152 of the measurement line 50, an enzyme reaction is performed, and then, at the position P153, a photometric measurement is performed by the measurement unit 110. Then, the measurement in the normal mode is ended.

(Measurement Method—Time Reduction Mode)

Next, the measurement method in the time reduction mode is described. First, at the positions P2 and P3 of the first reaction line 30, a treatment similar to that in the normal mode is performed to the point where the content of the cuvette is mixed by the mixer. After this mixing, at the positions P17 and P18, magnetic particles are collected by the magneto collectors 60 and 61, respectively, then, at the positions P19 and P20, the magnetic particles are washed off by the washer 80, then, at the position P21, the content of the cuvette is mixed by the mixer 92, then, at the positions P23 and P24, the magnetic particles are collected by the magneto collectors 62 and 63, respectively, and then, at the positions P25 and P26, the magnetic particles are washed off again by the washer 81.

Then, at the position P27, a labeled body solution is dispensed to the cuvette from a conjugate solution bottle placed in the reagent containing space 7 by the second reagent dispenser 14, then, at the position P28, the content of the cuvette is mixed by the mixer 93, then, at the positions P44 and P45, the magnetic particles are collected by the magneto collectors 64 and 65, respectively, and then, at the positions P46 and P47, the magnetic particles are washed off again by the washer 82. Then, at the position P48, the content of the cuvette is mixed by the mixer 94, then, at the positions P50 and P51, the magnetic particles are collected by the magneto collectors 66 and 67, respectively, and then, at the positions P52 and P53, the magnetic particles are washed off again by the washer 83.

Then, at the position P54, a substrate solution is dispensed to the cuvette by the substrate dispenser 100, then the content of the cuvette is mixed to disperse the magnetic particles, then, at the position P55, the cuvette is conveyed to the position P121 of the measurement line 50 by the second cuvette conveyer 9, then, at the positions P121 to P152 of the measurement line 50, an enzyme reaction is performed, and then, at the position P153, a photometric measurement is performed by the measurement unit 110. Then, the measurement in the time reduction mode is ended.

(Measurement Method—Mutual Relation Between Normal Mode and Time Reduction Mode)

Next, the mutual relation between the normal mode and the time reduction mode is described. First, in the normal mode, as described above, part of the reaction step is performed in the first reaction line 30, and the rest of the reaction step is performed in the second reaction line 40. Note that, since, in both the first reaction line 30 and the second reaction line 40, intermittent conveying is performed at 15 second intervals, a cuvette having been treated in the first and second reaction steps in the normal mode is discharged from the second reaction line 40 at 15 second intervals at the maximum. On the other hand, in the time reduction mode, all of the reaction steps are performed only in the first reaction line 30. Note that, since, in the first reaction line 30, intermittent conveying is performed at 15 second intervals, a cuvette having been treated in the first and second reaction steps in the time reduction mode is discharged from the first reaction line 30 at 15 second intervals at the maximum.

Accordingly, when measurement is performed in a mode that is a mixture of the normal mode and the time reduction mode with the number of cuvettes to be measured in the normal mode equal to the number of cuvettes to be measured in the time reduction mode, a cuvette to be measured in the time reduction mode is discharged from the first reaction line 30 at 15 second intervals at the maximum, and a cuvette to be measured in the normal mode is discharged from the second reaction line 40 at 15 second intervals at the maximum. Note that, since the measurement line 50 conveys cuvettes at 7.5 second intervals, half of 15 second intervals, the measurement line 50 can alternately accept the cuvette discharged from the first reaction line 30 at 15 second intervals at the maximum and the cuvette discharged from the second reaction line 40 at 15 second intervals at the maximum.

Figure 4:
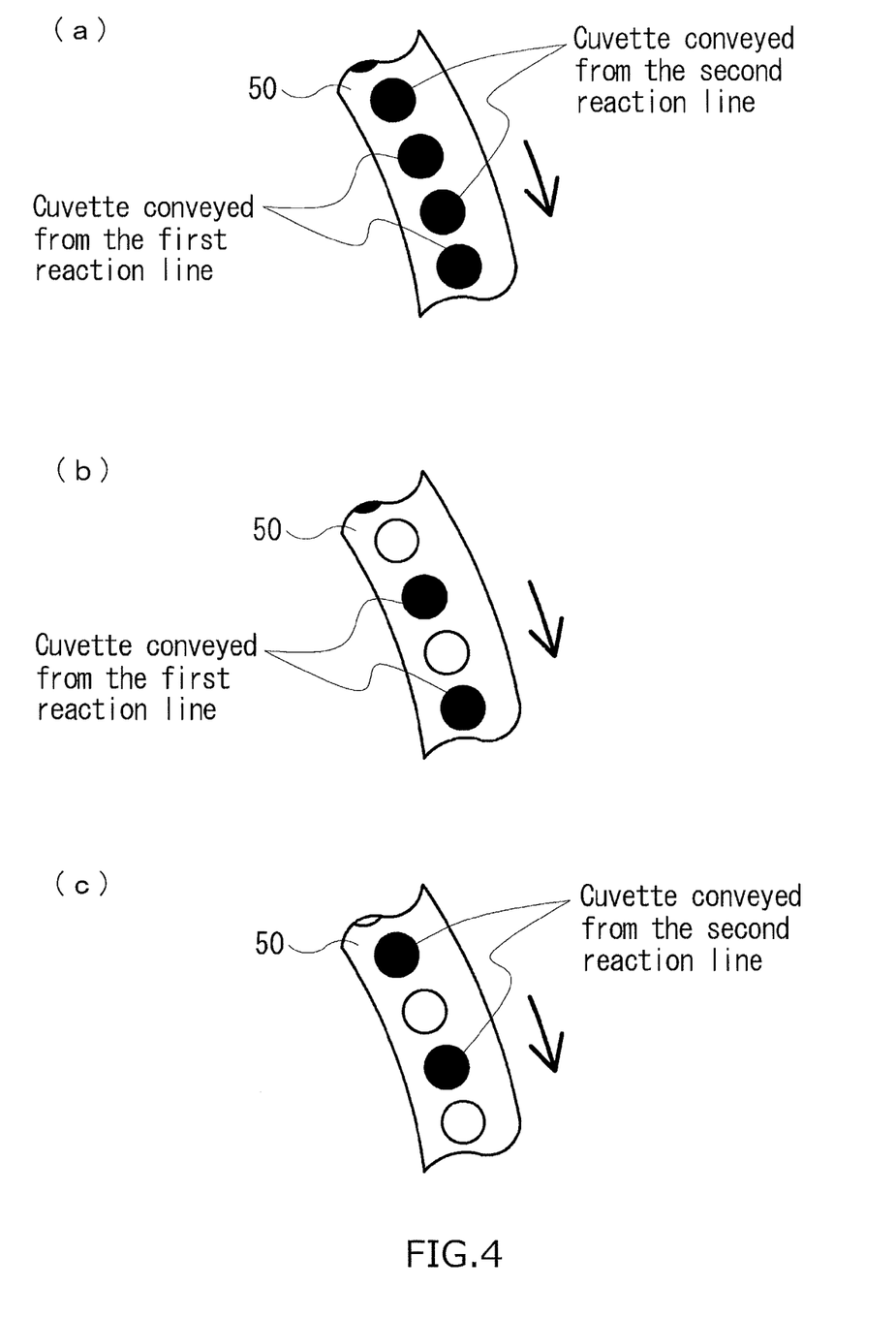
FIG. 4 A main part enlarged plan view of a measurement line on which a cuvette is placed.

FIG. 4 is a main part enlarged plan view of the measurement line 50 on which a cuvette is placed. FIG. 4(a) shows a placement of cuvettes in a mode that is a mixture of the normal mode and the time reduction mode at equal rate. FIG. 4(b) shows a placement of cuvettes in the time reduction mode only. FIG. 4(c) shows a placement of cuvettes in the normal mode only.

With the mixture of the normal mode and the time reduction mode at equal rate, as shown in FIG. 4(a), in the measurement line 50, a cuvette having been treated in the second reaction line 40 and a cuvette having been treated in the first reaction line 30 are alternately and continuously placed. Thus, the first reaction line 30 and the second reaction line 40 can work at their respective shortest convey intervals, which allows the measurement to be performed without decreasing the throughput of 15 second intervals.

On the other hand, in the normal mode only, as shown in FIG. 4(c), since a cuvette having been treated in the first reaction line 30 is not placed on the measurement line 50, only a cuvette having been treated in the second reaction line 40 is placed at one-cuvette intervals. Or, in the time reduction mode only, as shown in FIG. 4(b), since a cuvette having been treated in the second reaction line 40 is not placed on the measurement line 50, only a cuvette having been treated in the first reaction line 30 is placed at one-cuvette intervals.

(Effect of First Embodiment)

Thus, according to the first embodiment, in the first reaction line 30, a sample is reacted with a reagent while a cuvette is conveyed at the first convey speed, and, in the second reaction line 40, a sample is reacted with a reagent while a cuvette is conveyed at the second convey speed, and then, in the measurement line 50, a predetermined material included in the samples within these cuvettes are measured while the cuvettes are conveyed at the third convey speed higher than the first and second convey speeds. So, the reaction containers in which the samples are reacted with the reagents in the first reaction line 30 and the second reaction line 40 can be measured without delay, which eliminates the need for matching the convey speed in reaction with the convey speed in measurement, allowing the throughput of the first reaction line 30 and the second reaction line 40 to be prevented from decreasing.

Furthermore, since the third convey speed is set to a common multiple of the first convey speed and the second convey speed, a cuvette conveyed from the first reaction line 30 to the measurement line 50 and a cuvette conveyed from the second reaction line 40 to the measurement line 50 can be prevented from being simultaneously conveyed to the same vacant position in the measurement line 50 and interfering with each other.

Furthermore, since the first convey speed and the second convey speed are set to be equal to each other and the third convey speed is set to an integer multiple of the first convey speed and the second convey speed, a cuvette conveyed from the first reaction line 30 to the measurement line 50 and a cuvette conveyed from the second reaction line 40 to the measurement line 50 can be prevented from being simultaneously conveyed to the same vacant position in the measurement line 50 and interfering with each other.

Furthermore, a predetermined material included in a sample on which all of the immune reaction in the normal mode has been performed in the first reaction line 30 and the second reaction line 40 and a sample on which all of the immune reaction in the time reduction mode has been performed in the first reaction line 30 can be measured without delay in the measurement line 50, which allows the throughput of the first reaction line 30 and the second reaction line 40 to be prevented from decreasing even in a mixture of the normal mode and the time reduction mode.

Second Embodiment

Next, a second embodiment is described. In the second embodiment, only one reaction line is provided. Unless otherwise specified, the second embodiment has almost the same configuration as that of the first embodiment. So, for almost the same components as those of the first embodiment, the same reference numerals or names as used in the first embodiment are appropriately used and descriptions on those components are omitted (the same shall apply to third and fourth embodiments).

(Configuration)

Figure 5:
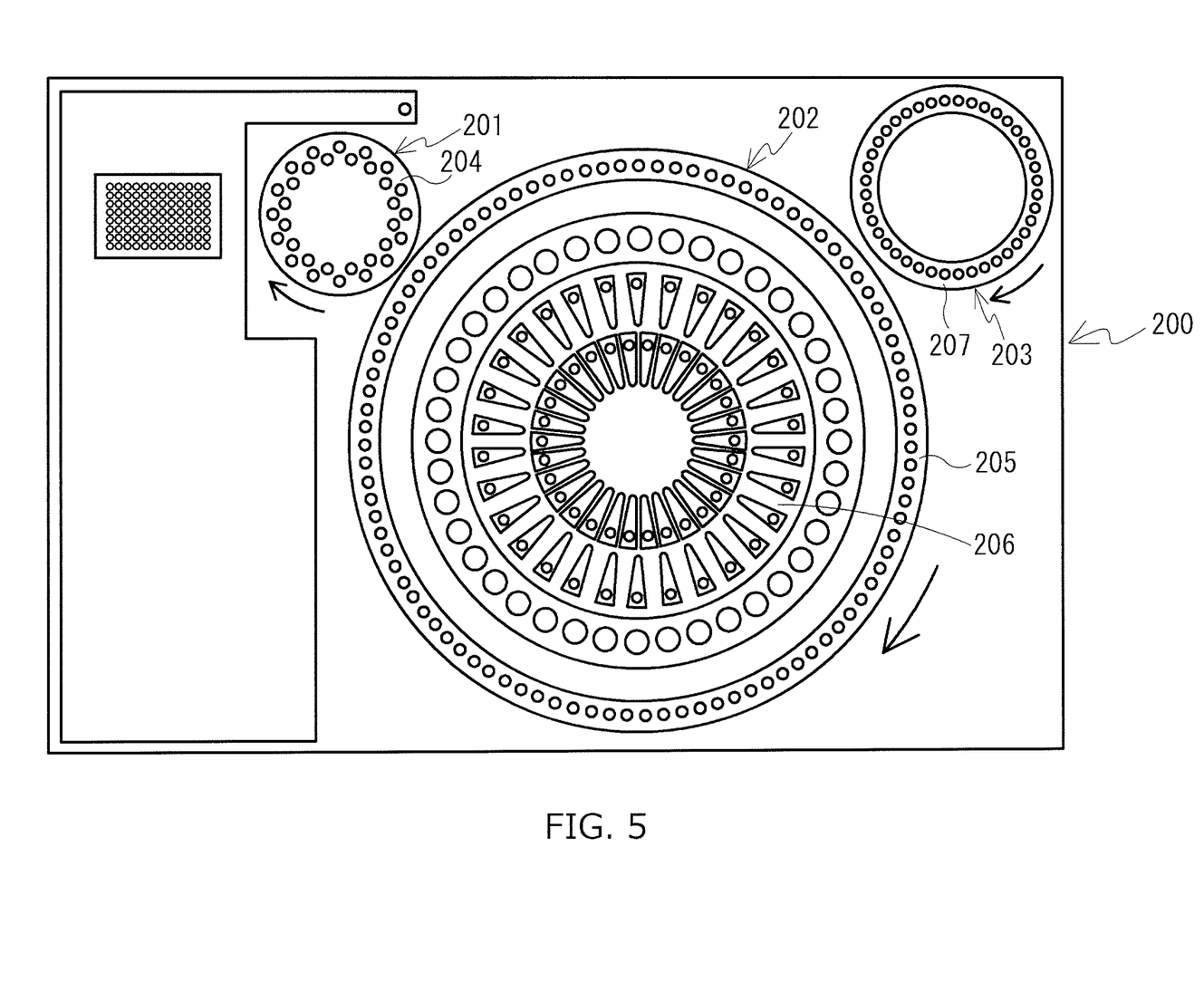
FIG. 5 A main part plan view of a measurement device in accordance with a second embodiment.

FIG. 5 is a main part plan view of a measurement device in accordance with the second embodiment. A measurement device 200 includes a first table 201, a second table 202 and a third table 203 in place of the first table 15 and the second table 16 of the first embodiment. The first table 201 includes a pretreatment line 204. The second table 202 includes a reaction line 205 and a reagent containing space 206. The third table 203 includes a measurement line 207. Note that, in FIG. 5, a conveyer for conveying a cuvette between the lines and a reagent dispenser for dispensing a reagent are not shown (the same shall apply to FIGS. 6 and 7 described later).

The pretreatment line 204 is a line for performing pretreatment and dilution on a sample. The reaction line 205 is a line for reacting a sample with magnetic particles or reacting a product of the reaction between the sample and the magnetic particles with a labeled antibody. The reaction line 205 intermittently conveys a cuvette illustrated clockwise at 15 second intervals. The measurement line 207 is a line for detecting an enzyme reaction between a labeled antibody and a substrate and detecting the light amount of light generated by chemiluminescence from a product of the enzyme reaction. The measurement line 207 intermittently conveys a cuvette illustrated clockwise at 7.5 second intervals.

(Measurement Method)

In the thus configured measurement device 200, a cuvette having been pretreated in the pretreatment line 204 is conveyed to the reaction line 205. In the reaction line 205, for a cuvette in the normal mode, the first and second reaction steps are performed while the cuvette rotates about one revolution in the reaction line 205, then the cuvette is conveyed to the measurement line 207 in which the enzyme reaction step and the measurement step are performed. On the other hand, for a cuvette in the time reduction mode, the first and second reaction steps are performed while the cuvette rotates about a half revolution in the reaction line 205, then the cuvette is conveyed to the measurement line 207 in which the enzyme reaction step and the measurement step are performed.

For example, when measurement is performed in a mixture of the normal mode and the time reduction mode, at the initial position of the reaction line 205, a cuvette in the normal mode and a cuvette in the time reduction mode are alternately placed, then the cuvette in the normal mode is conveyed from near the final position of the reaction line 205 to the measurement line 207 at 15 second intervals at the maximum, and the cuvette to be measured in the time reduction mode is conveyed from near the central position of the reaction line 205 to the measurement line 207 at 15 second intervals at the maximum.

Since the measurement line 207 conveys a cuvette at 7.5 second intervals, half of 15 second intervals, the measurement line 207 can alternately accept the cuvette in the normal mode discharged from the reaction line 205 at 15 second intervals at the maximum and the cuvette in the time reduction mode discharged from the reaction line 205 at 15 second intervals at the maximum.

(Effect of Second Embodiment)

Thus, according to the second embodiment, even when only one reaction line 205 is provided, both a cuvette discharged from the reaction line 205 in the normal mode and a cuvette discharged from the reaction line 205 in the time reduction mode can be accepted by the measurement line 207 without delay, which allows the throughput of the reaction line 205 to be prevented from decreasing.

Third Embodiment

Next, a third embodiment is described. In the third embodiment, the first reaction line and the second reaction line are provided as linear convey mechanisms different from each other.

(Configuration)

Figure 6:
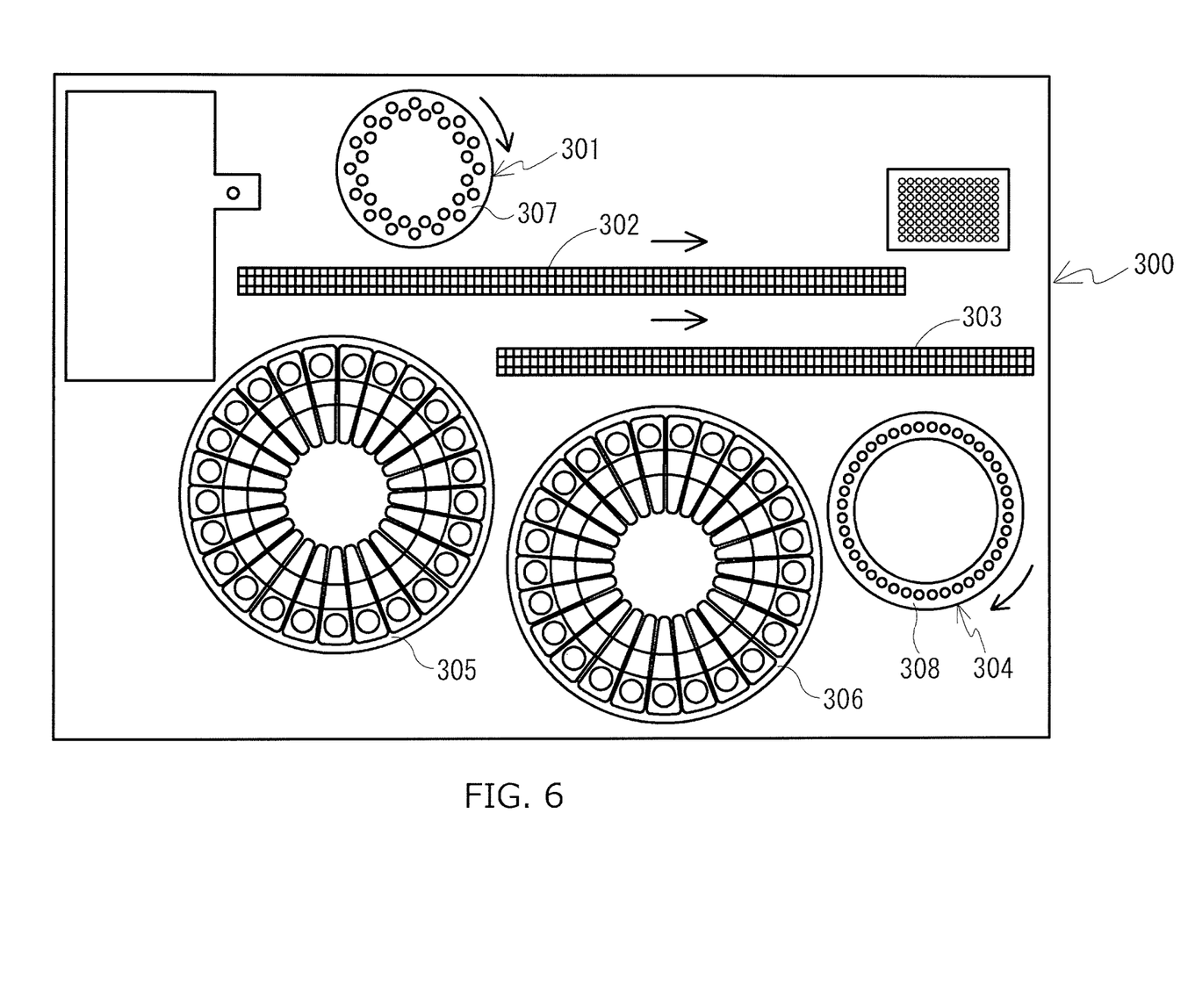
FIG. 6 A main part plan view of a measurement device in accordance with a third embodiment.

FIG. 6 is a main part plan view of a measurement device in accordance with the third embodiment. A measurement device 300 includes a first table 301, a first reaction line 302, a second reaction line 303, a second table 304, and reagent containing spaces 305 and 306 in place of the first table 15 and the second table 16 of the first embodiment. The first table 301 includes a pretreatment line 307. The second table 304 includes a measurement line 308.

The pretreatment line 307 is a line for performing pretreatment and dilution on a sample. The first reaction line 302 and the second reaction line 303 are lines for reacting a sample with magnetic particles or reacting a product of the reaction between the sample and the magnetic particles with a labeled antibody. In this example, these lines are configured as a linear convey mechanism for linearly conveying a cuvette along the horizontal direction, which intermittently convey a cuvette in the illustrated arrow direction at 15 second intervals. The measurement line 308 is a line for detecting an enzyme reaction between a labeled antibody and a substrate and detecting the light amount of light generated by chemiluminescence from a product of the enzyme reaction. The measurement line 308 intermittently conveys a cuvette illustrated clockwise at 7.5 second intervals.

(Measurement Method)

In the thus configured measurement device 300, a cuvette having been pretreated in the pretreatment line 307 is conveyed to the first reaction line 302. In the first reaction line 302, for a cuvette in the normal mode, the first reaction step is performed while the cuvette travels from the initial position to around the halfway position of the first reaction line 302, then the cuvette is conveyed to the second reaction line 303 and the second reaction step is performed while the cuvette travels from the initial position to near the final position of the second reaction line 303, and then the cuvette is conveyed to the measurement line 308 in which the enzyme reaction step and the measurement step are performed. On the other hand, for a cuvette in the time reduction mode, the first and second reaction steps are performed while the cuvette travels from the initial position to near the final position of the first reaction line 302, then the cuvette is conveyed to the measurement line 308 in which the enzyme reaction step and the measurement step are performed.

For example, when measurement is performed in a mixture of the normal mode and the time reduction mode, at the initial position of the first reaction line 302, a cuvette in the normal mode and a cuvette in the time reduction mode are alternately placed, then the cuvette in the normal mode is conveyed from near the final position of the second reaction line 303 to the measurement line 308 at 15 second intervals at the maximum, and the cuvette to be measured in the time reduction mode is conveyed from near the final position of the first reaction line 302 to the measurement line 308 at 15 second intervals at the maximum.

Since the measurement line 308 conveys a cuvette at 7.5 second intervals, half of 15 second intervals, the measurement line 308 can alternately accept the cuvette in the time reduction mode discharged from the first reaction line 302 at 15 second intervals at the maximum and the cuvette in the normal mode discharged from the second reaction line 303 at 15 second intervals at the maximum.

(Effect of Third Embodiment)

Thus, according to the third embodiment, even when the first reaction line 302 and the second reaction line 303 are provided as linear convey mechanisms different from each other, both the cuvette in the time reduction mode discharged from the first reaction line 302 and the cuvette in the normal mode discharged from the second reaction line 303 can be accepted by the measurement line 308 without delay, which allows the throughput of the first reaction line 302 and the second reaction line 303 to be prevented from decreasing.

Fourth Embodiment

Next, a fourth embodiment is described. In the fourth embodiment, the first reaction line is provided on a disk-shaped table, and the second reaction line is provided as a linear convey mechanism.

(Configuration)

Figure 7:
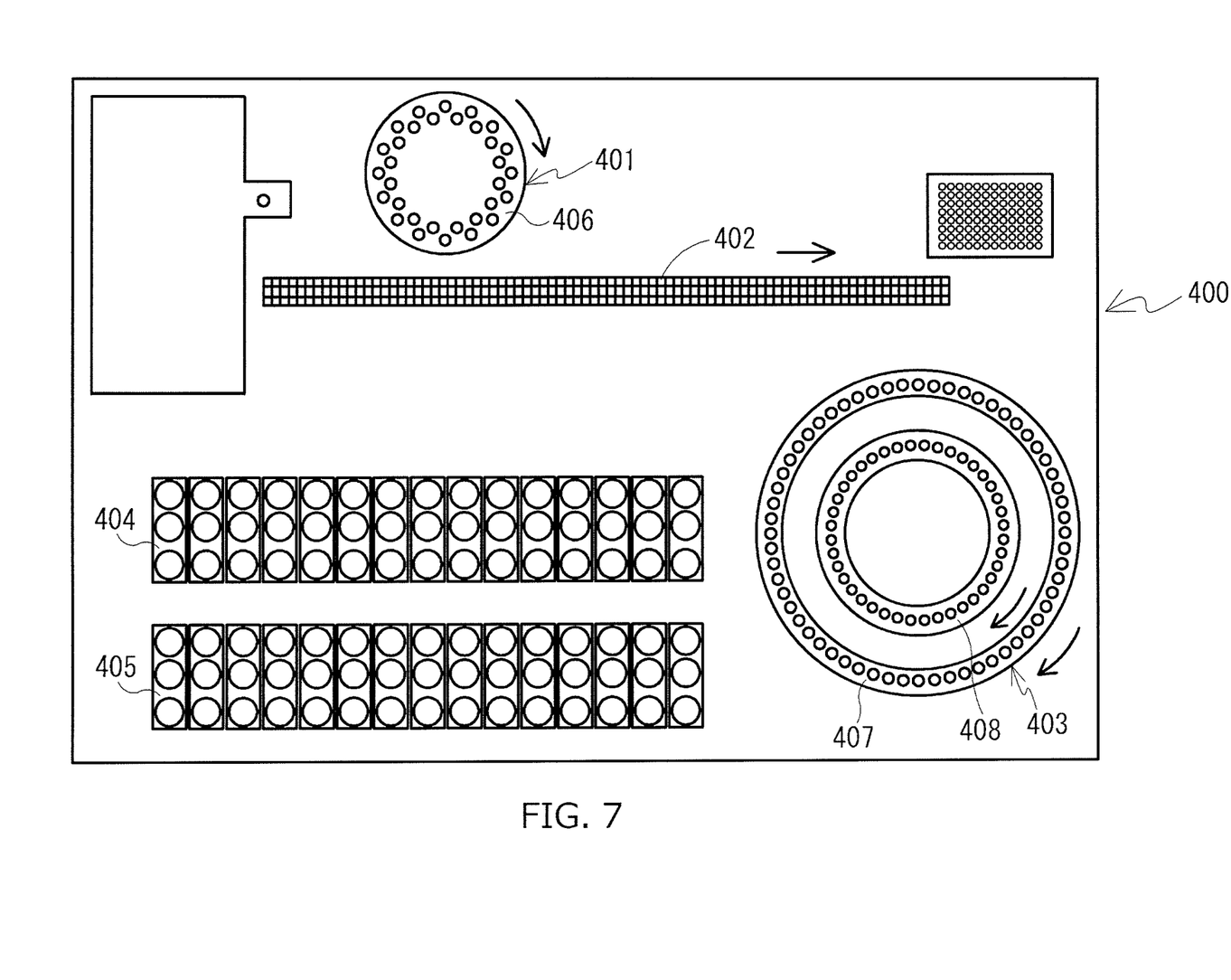
FIG. 7 A main part plan view of a measurement device in accordance with a fourth embodiment.

FIG. 7 is a main part plan view of a measurement device in accordance with the fourth embodiment. A measurement device 400 includes a first table 401, a first reaction line 402, a second table 403, and reagent containing spaces 404 and 405 in place of the first table 15 and the second table 16 of the first embodiment. The first table 401 includes a pretreatment line 406. The second table 403 includes a second reaction line 407 placed in the outer periphery and a measurement line 408 placed in the inner periphery.

The pretreatment line 406 is a line for performing pretreatment and dilution on a sample. The first reaction line 402 and the second reaction line 407 are lines for reacting a sample with magnetic particles or reacting a product of the reaction between the sample and the magnetic particles with a labeled antibody. In this example, the second reaction line 407 is configured as a rotating convey mechanism for intermittently conveying a cuvette illustrated clockwise at 15 second intervals, as with the first reaction line 30 of the first embodiment. The first reaction line 402 is configured as a linear convey mechanism for linearly conveying a cuvette along the horizontal direction, as with the second reaction line 303 of the third embodiment, and intermittently conveys a cuvette in the illustrated arrow direction at 15 second intervals. The measurement line 408 is a line for detecting an enzyme reaction between a labeled antibody and a substrate and detecting the light amount of light generated by chemiluminescence from a product of the enzyme reaction. The measurement line 408 intermittently conveys a cuvette illustrated clockwise at 7.5 second intervals.

(Measurement Method)

In the thus configured measurement device 400, a cuvette having been pretreated in the pretreatment line 406 is conveyed to the first reaction line 402. In the first reaction line 402, for a cuvette in the normal mode, the first reaction step is performed while the cuvette travels from the initial position to around the halfway position of the first reaction line 402, then the cuvette is conveyed to the second reaction line 407 and the second reaction step is performed while the cuvette travels from the initial position to near the final position of the second reaction line 407, and then the cuvette is conveyed to the measurement line 408 in which the enzyme reaction step and the measurement step are performed. On the other hand, for a cuvette in the time reduction mode, the first and second reaction steps are performed while the cuvette travels from the initial position to near the final position of the first reaction line 402, then the cuvette is conveyed to the measurement line 408 in which the enzyme reaction step and the measurement step are performed.

For example, when measurement is performed in a mixture of the normal mode and the time reduction mode, at the initial position of the first reaction line 402, a cuvette in the normal mode and a cuvette in the time reduction mode are alternately placed, then the cuvette in the normal mode is conveyed from near the final position of the second reaction line 407 to the measurement line 408 at 15 second intervals at the maximum, and the cuvette to be measured in the time reduction mode is conveyed from near the final position of the first reaction line 402 to the measurement line 408 at 15 second intervals at the maximum.

Since the measurement line 408 conveys a cuvette at 7.5 second intervals, half of 15 second intervals, the measurement line 408 can alternately accept the cuvette in the time reduction mode discharged from the first reaction line 402 at 15 second intervals at the maximum and the cuvette in the normal mode discharged from the second reaction line 407 at 15 second intervals at the maximum.

(Effect of Fourth Embodiment)

Thus, according to the fourth embodiment, even when the second reaction line 407 is provided on a disk-shaped table, and the first reaction line 402 is provided as a linear convey mechanism, both the cuvette in the time reduction mode discharged from the first reaction line 402 and the cuvette in the normal mode discharged from the second reaction line 407 can be accepted by the measurement line 408 without delay, which allows the throughput of the first reaction line 402 and the second reaction line 407 to be prevented from decreasing.

[III] VARIATION ON EMBODIMENTS

The embodiments in accordance with the invention have been described above. However, any appropriate modification and variation can be made to the specific configuration and means of the invention without departing from the scope of the technical spirit of the invention according to the claims. Such a variation is described below.

(On Problems to be Solved and Advantages of the Invention)

First, the problems to be solved by the invention and the advantages of the invention are not limited to what has been described above. The invention may also solve a problem that has not been described above and provide an advantage that has not been described above, or may also solve only part of the problems that has been described above and provide only part of the advantages that has been described above.

(On Pretreatment Line and Pretreatment Step)

The pretreatment step may be omitted depending on the type of the measurement method to be performed. In this case, the pretreatment line 20 may be omitted. Or, even when the pretreatment step is performed, the pretreatment step may be performed in the first reaction line 30 or the second reaction line 40 and the pretreatment line 20 may be omitted.

(On Line Configuration)

The pretreatment line 20, the first reaction line 30, the second reaction line 40 and the measurement line 50 may be configured to be in any suitable line shape in addition to a plane disk shape and a plane linear shape as described in the above embodiments. For example, a line shape in which the steps are performed while a cuvette is conveyed along the vertical direction may be used. Furthermore, lines having plane shapes and configurations different from one another may be combined for the pretreatment line 20, the first reaction line 30, the second reaction line 40 and the measurement line 50.

(On Measurement Mode)

In the above embodiments, two measurement modes including the normal mode and the time reduction mode are used for the measurement. However, only one mode or three or more modes may be used. For example, as an example of the measurement only in one mode, the first reaction line 30 and the second reaction line 40 may also be configured as lines in each of which only the reaction in the time reduction mode is performed at 15 second intervals so that a cuvette discharged from the first reaction line 30 at 15 second intervals and a cuvette discharged from the second reaction line 40 at 15 second intervals are conveyed in the measurement line 50 at 7.5 second intervals. Or, as an example of performing measurement in three modes, first to third reaction lines each for performing reaction at 30 second intervals may be provided in which the time reduction mode is performed only in the first reaction line 30, the normal mode is performed in the first reaction line 30 and the second reaction line 40, and an extension mode for performing reaction taking a time longer than that for the normal mode is performed in the first to third reaction lines so that cuvettes discharged from the first to third reaction lines at 30 second intervals are conveyed in the measurement line 50 at 10 second intervals.

(On Convey Speed)

In the above embodiments, the first convey speed of the first reaction line 30 and the second convey speed of the second reaction line 40 are set to be equal to each other, then the third convey speed of the measurement line 50 is set to be twice the first convey speed and the second convey speed. However, the convey speeds can be set without being limited to the above relation.

For example, the third convey speed of the measurement line 50 is not limited to the twice of the first convey speed of the first reaction line 30 and the second convey speed of the second reaction line 40, but at least only needs to be higher than the first convey speed and the second convey speed. As a specific example, the first, second and third convey speeds may be one step per 40 seconds (60 second intervals), one step per 30 seconds (40 second intervals) and one step per 10 seconds (10 second intervals), respectively. In this case, a cuvette discharged from the first reaction line 30 and a cuvette discharged from the second reaction line 40 can be conveyed to the measurement line 50 without delay. However, in this case, a vacant position exists in the measurement line 50. Furthermore, a cuvette discharged from the first reaction line 30 and a cuvette discharged from the second reaction line 40 may need to be conveyed to the measurement line 50 at the same time. In this case, the cuvettes may be allowed to be conveyed to different vacant positions in the measurement line 50 to prevent the cuvettes from interfering with each other.

Or, in order to prevent such interference between the cuvettes, the third convey speed is preferably set to a common multiple of the first and second convey speeds. For example, the first, second and third convey speeds may be one step per 45 seconds (45 second intervals), one step per 30 seconds (30 second intervals) and one step per 15 seconds (15 second intervals), respectively. Also, for the similar reason, when the first convey speed of the first reaction line 30 and the second convey speed of the second reaction line 40 are set to be equal to each other, the third convey speed of the measurement line 50 is preferably set to be an integer multiple of the first convey speed and the second convey speed.

Particularly, in order to increase space efficiency of the measurement line 50, the third convey speed is preferably set to a least common multiple of the first and second convey speeds (the twice when the first convey speed of the first reaction line 30 and the second convey speed of the second reaction line 40 are set to be equal to each other).

(On Convey Method)

In the above embodiments, a cuvette is intermittently conveyed. However, a cuvette may be continuously conveyed without being limited to be intermittently conveyed.

DESCRIPTION OF REFERENCE NUMERALS AND SIGNS 1, 200, 300, 400 measurement device
2 base surface
3 measurement mechanism
4 cuvette feeder
5 sample feeder
6 tip feeder
7, 206, 305, 306, 404, 405 reagent containing space
8 first cuvette conveyer
9 second cuvette conveyer
10 third cuvette conveyer
11 sample conveyer
12 tip conveyer
13 first reagent dispenser
14 second reagent dispenser
15, 201, 301, 401 first table
16, 202, 304, 403 second table
20, 204, 307, 406 pretreatment line
30, 302, 402 first reaction line
40, 303, 407 second reaction line
50, 207, 308, 408 measurement line
60-75 magneto collector
80-87 wash solution discharger/drawer
90-97 mixer
100, 101 substrate dispenser
110 measurement unit
203 third table
205 reaction line

The invention claimed is:

1. A measurement device for measuring a predetermined material included in a sample contained in a reaction container comprising:
   at least one reaction line for reacting the sample with a reagent within the reaction container, the reaction line conveying the reaction container at a predetermined convey speed;
   one measurement line measuring the predetermined material included in the sample reacted with the reagent within the reaction container in the reaction line, the measurement line conveying the reaction container conveyed from the reaction line at a predetermined convey speed that is higher than the convey speed of the reaction line; and
   a control unit that runs a measurement program the measurement program configured to convey the reaction container on the reaction line at the predetermined convey speed of the reaction line and to convey the reaction container conveyed from the reaction line at the predetermined speed of the measurement line.

2. The measurement device according to claim 1,
   wherein the reaction line comprises:
   a first reaction line, wherein the measurement program is configured to convey the reaction container at a first convey speed; and
   a second reaction line, wherein the measurement program is configured to convey the reaction container at a second convey speed, and
   wherein the measurement line is
   a measurement line measuring the predetermined material included in the sample reacted with the reagent within the reaction container in the first reaction line and the sample reacted with the reagent within the reaction container in the second reaction line, the measurement program configured to convey the reaction containers on the measurement line at a third convey speed that is higher than the first convey speed and the second convey speed.

3. The measurement device according to claim 2,
   wherein the third convey speed is set to a common multiple of the first convey speed and the second convey speed.

4. The measurement device according to claim 3,
   wherein the first convey speed and the second convey speed are set to be equal to each other, and
   wherein the third convey speed is set to an integer multiple of the first convey speed and the second convey speed.

5. The measurement device according to claim 2, for performing measurement using immunoassay,
   wherein, as a reaction mode for performing immune reaction of the sample and the reagent within the reaction container, a normal mode for performing reaction in a predetermined reaction time and a time reduction mode for performing reaction in a predetermined reaction time that is shorter than that of the normal mode are provided,
   wherein the first reaction line is a line for performing part of the immune reaction in the normal mode and all of the immune reaction in the time reduction mode, wherein the second reaction line is a line for performing the rest of the immune reaction in the normal mode, and wherein the measurement line is a line for performing measurement on the sample on which all of the immune reaction in the normal mode has been performed in the first reaction line and the second reaction line and the sample on which all of the immune reaction in the time reduction mode has been performed in the first reaction line.

6. The measurement device according to claim 3, for performing measurement using immunoassay, wherein, as a reaction mode for performing immune reaction of the sample and the reagent within the reaction container, a normal mode for performing reaction in a predetermined reaction time and a time reduction mode for performing reaction in a predetermined reaction time that is shorter than that of the normal mode are provided, wherein the first reaction line is a line for performing part of the immune reaction in the normal mode and all of the immune reaction in the time reduction mode, wherein the second reaction line is a line for performing the rest of the immune reaction in the normal mode, and wherein the measurement line is a line for performing measurement on the sample on which all of the immune reaction in the normal mode has been performed in the first reaction line and the second reaction line and the sample on which all of the immune reaction in the time reduction mode has been performed in the first reaction line.

7. The measurement device according to claim 4, for performing measurement using immunoassay, wherein, as a reaction mode for performing immune reaction of the sample and the reagent within the reaction container, a normal mode for performing reaction in a predetermined reaction time and a time reduction mode for performing reaction in a predetermined reaction time that is shorter than that of the normal mode are provided, wherein the first reaction line is a line for performing part of the immune reaction in the normal mode and all of the immune reaction in the time reduction mode, wherein the second reaction line is a line for performing the rest of the immune reaction in the normal mode, and wherein the measurement line is a line for performing measurement on the sample on which all of the immune reaction in the normal mode has been performed in the first reaction line and the second reaction line and the sample on which all of the immune reaction in the time reduction mode has been performed in the first reaction line.

* * * * *